(12) United States Patent
Hopenfeld

(10) Patent No.: US 9,402,557 B2
(45) Date of Patent: Aug. 2, 2016

(54) HEART BEAT DETECTION BASED ON PERMISSIBLE SEQUENCE SEARCHING

(71) Applicant: Bruce Hopenfeld, Salt Lake City, UT (US)

(72) Inventor: Bruce Hopenfeld, Salt Lake City, UT (US)

( * ) Notice: Subject to any disclaimer, the term of this patent is extended or adjusted under 35 U.S.C. 154(b) by 77 days.

(21) Appl. No.: 14/296,559

(22) Filed: Jun. 5, 2014

(65) Prior Publication Data
US 2015/0005654 A1      Jan. 1, 2015

Related U.S. Application Data

(60) Provisional application No. 61/840,692, filed on Jun. 28, 2013, provisional application No. 61/884,018, filed on Sep. 28, 2013, provisional application No. 61/897,347, filed on Oct. 30, 2013, provisional application No. 61/921,668, filed on Dec. 30, 2013.

(51) Int. Cl.
| | |
|---|---|
| *A61B 5/0456* | (2006.01) |
| *A61B 5/046* | (2006.01) |
| *A61B 5/00* | (2006.01) |
| *A61B 5/0245* | (2006.01) |

(52) U.S. Cl.
CPC ............. *A61B 5/046* (2013.01); *A61B 5/0006* (2013.01); *A61B 5/0245* (2013.01); *A61B 5/0456* (2013.01)

(58) Field of Classification Search
CPC .... A61B 5/024; A61B 5/0452; A61B 5/0456; A61B 5/0468; A61B 5/046; A61B 5/0006; A61B 5/0245
USPC .................. 600/509, 516, 517, 521, 393
See application file for complete search history.

(56) References Cited

U.S. PATENT DOCUMENTS

2010/0004713 A1 *   1/2010   Warren .............. A61B 5/04525
                                                           607/17

OTHER PUBLICATIONS

Per Ola Borgesson et al, Adaptive QRS Detection Based on Maximum a Posterior Estimation, IEEE Trans. Biomedical Eng., 1982, 29:341-351.

* cited by examiner

*Primary Examiner* — Theodore Stigell
*Assistant Examiner* — Michael Carey
(74) *Attorney, Agent, or Firm* — Bruce Hopenfeld

(57) ABSTRACT

A method for detecting heart beats within a cardiac signal is disclosed. A cardiac signal is acquired and segmented. Peak detection is performed within each segment. A search within the detected peaks is performed to locate physiologically permissible peak sequences. A particular peak sequence is selected based on feature space criteria or interpeak temporal regularity criteria or both.

11 Claims, 16 Drawing Sheets

Fig. 11

For all sequences with a RRM1 value >= 1, group RR intervals into 50ms clusters and associate each cluster with the max RRM1 value within the cluster; sort the cluster scores — 620

For all sequences with a RRM2 value >= 0, group RR intervals into 50ms clusters and associate each cluster with the max RRM2 value within the cluster; sort the cluster scores — 622

Fig. 12

For each of the candidate *RR* intervals in the current segment (time t), the path through the prior two sets of segment RR intervals is found that minimizes the second derivative, i.e., for *RR(t)*, the values of y and z are found that minimize $RR_x(t)'' = |RR_x(t) - 2*RR_y(t-1) + RR_z(t-2)|$. — 900

$Trscore1_x = (|RR_x(t) - RR_y(t-1)| + |RR_y(t-1) - RR_z(t-2)|)/2$ — 902

$Trscore2_x = |RR_x(t) - RRu(t-1)|$ — 904

Fig. 14
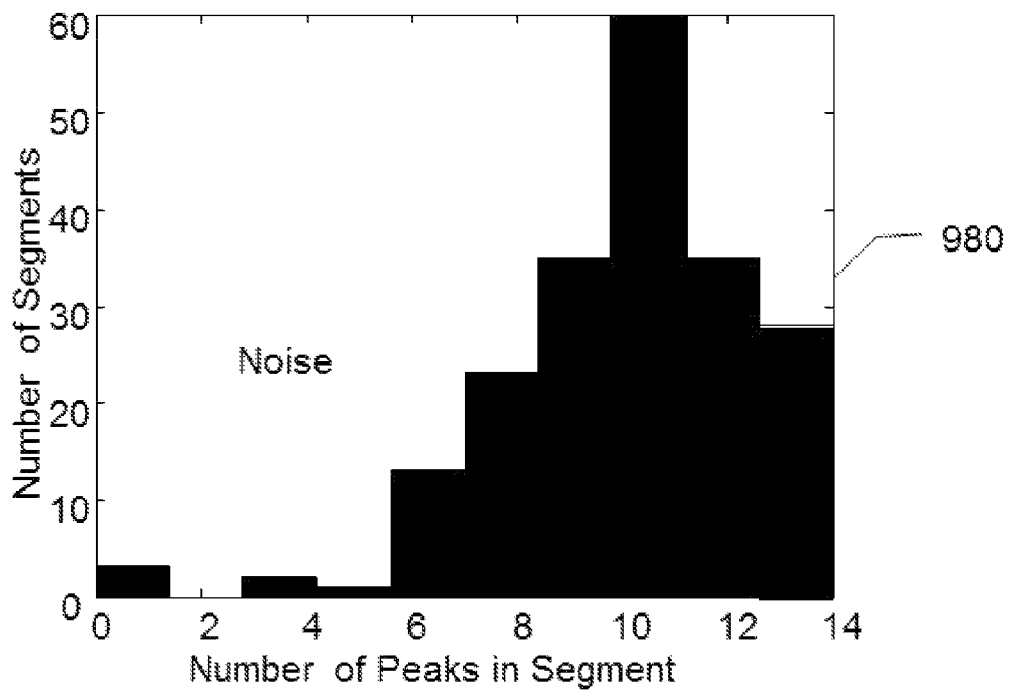
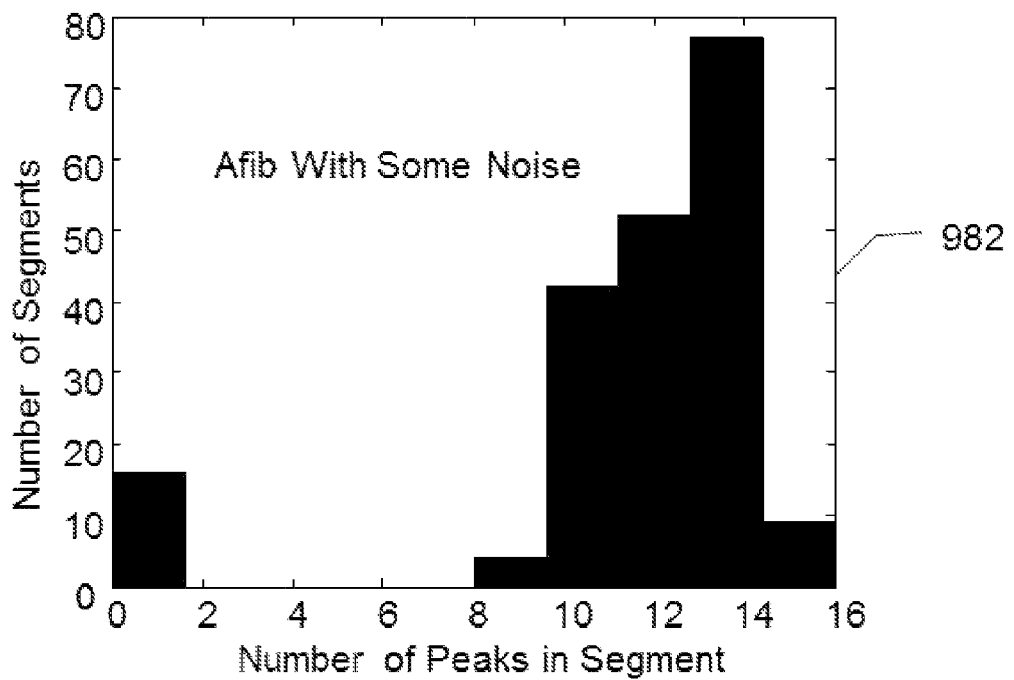

Fig. 15
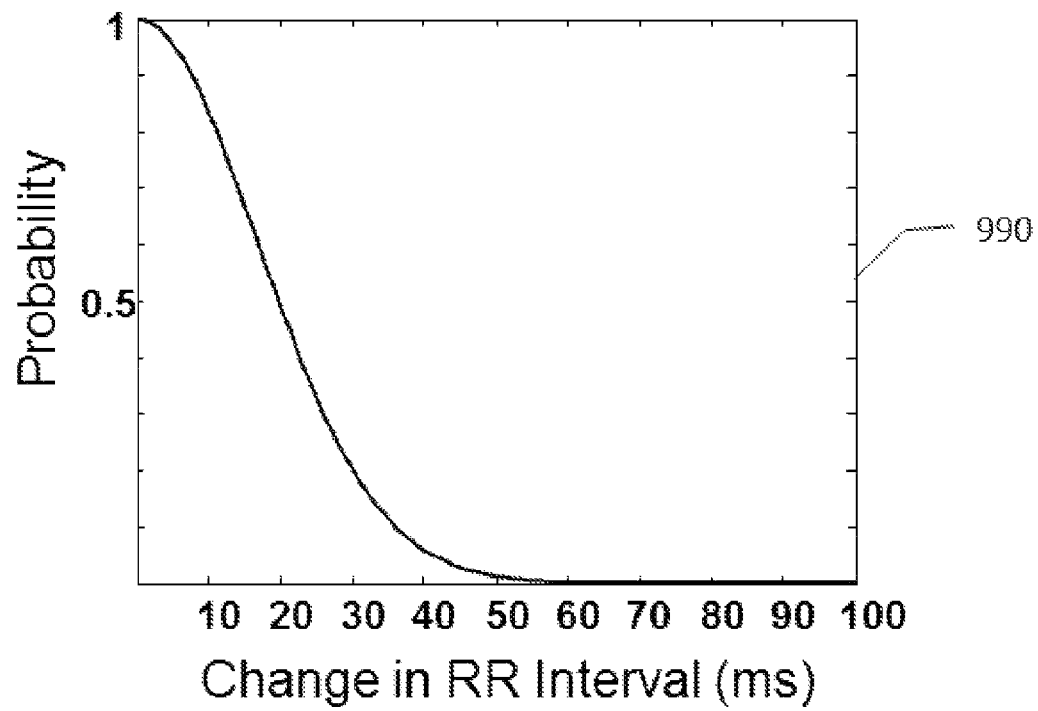
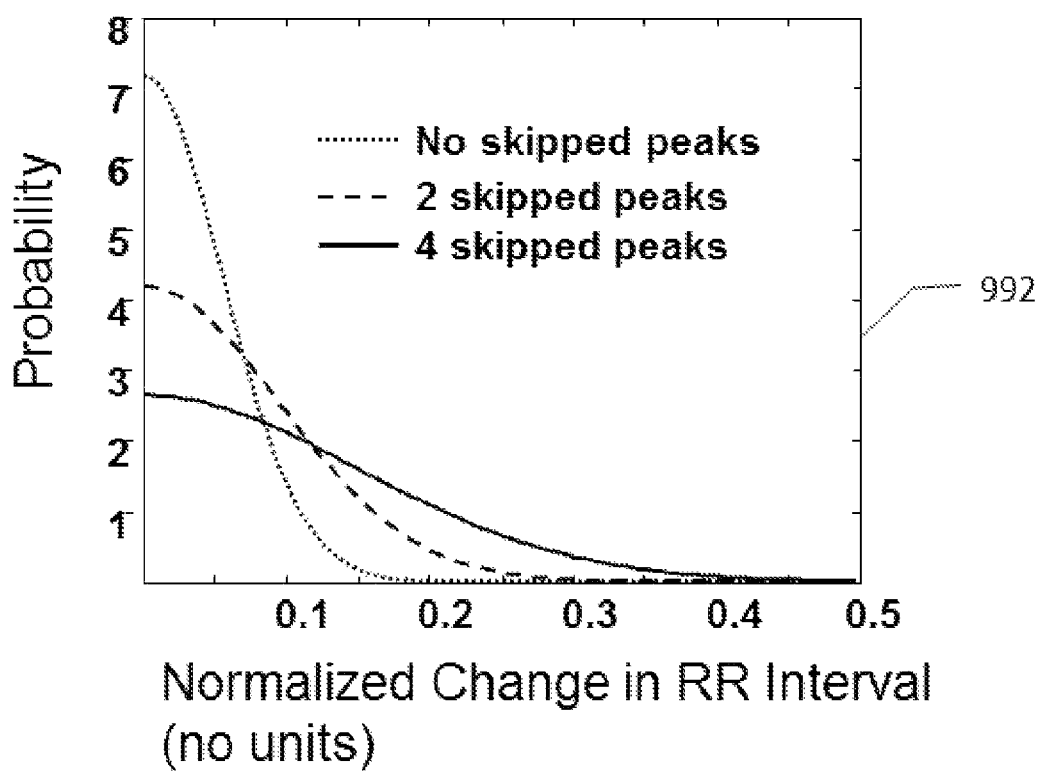

US 9,402,557 B2

HEART BEAT DETECTION BASED ON PERMISSIBLE SEQUENCE SEARCHING

PRIORITY CLAIM

This application claims priority to: U.S. Provisional Patent Application Ser. No. 61/840,692, filed on Jun. 28, 2013; U.S. Provisional Patent Application Ser. No. 61/884,018, filed on Sep. 28, 2013; U.S. Provisional Patent Application Ser. No. 61/897,347, filed on Oct. 30, 2013; and U.S. Provisional Patent Application Ser. No. 61/921,668, filed on Dec. 30, 2013.

FIELD OF INVENTION

The invention pertains primarily to cardiac monitoring, and in particular heart rate estimation and atrial fibrillation detection.

BACKGROUND

The continued evolution of wearable sensors and portable electronics will likely result in the substantial growth of long term day-to-day cardiac monitoring. Important aspects of cardiac monitoring include the estimation of heart rate and the detection of atrial fibrillation. Despite the advances in wearable sensors, noise remains a significant problem.

SUMMARY

One aspect of the invention pertains to a method for detecting heartbeats within a cardiac signal that is received from a sensor. The method includes detecting a plurality of peaks within a segment of the cardiac signal and then searching within the plurality of peaks for a set of physiologically permissible sequences. The search is performed such that the set of physiologically permissible sequences includes all physiologically permissible sequences within a subset of the plurality of peaks.

A probability based score is then assigned to each of a subset of the set of physiologically permissible sequences, with sequences that are more unlikely to be random receiving higher scores. The likelihood of a sequence being non-random is preferably determined by at least one of the following: 1) the tightness of the clustering of one or more features (e.g. maximum absolute slope) of the peaks in the sequence; or 2) the regularity of the inter-peak time intervals in the sequence.

BRIEF DESCRIPTION OF THE DRAWINGS

FIG. 11 shows steps associated with grouping sequences for the purposes of performing RR interval trend analysis.

FIG. 12 shows steps associated with scoring sequences according to RR interval trend.

FIG. 14 shows exemplary histograms of maximum sequence length for both atrial fibrillation sequences and pure noise sequences.

FIG. 15 shows plots of probability distributions for changes in RR interval in the case where there are no skipped beats and in the cases where there are different numbers of skipped beats.

DETAILED DESCRIPTION

Matlab notation is generally used herein.

The present invention will generally be described with reference to electrocardiographic signals. However, the principles herein are directly applicable to any type of cardiac signal that is characterized by having at least one distinct peak for each cardiac cycle.

Figure 1:
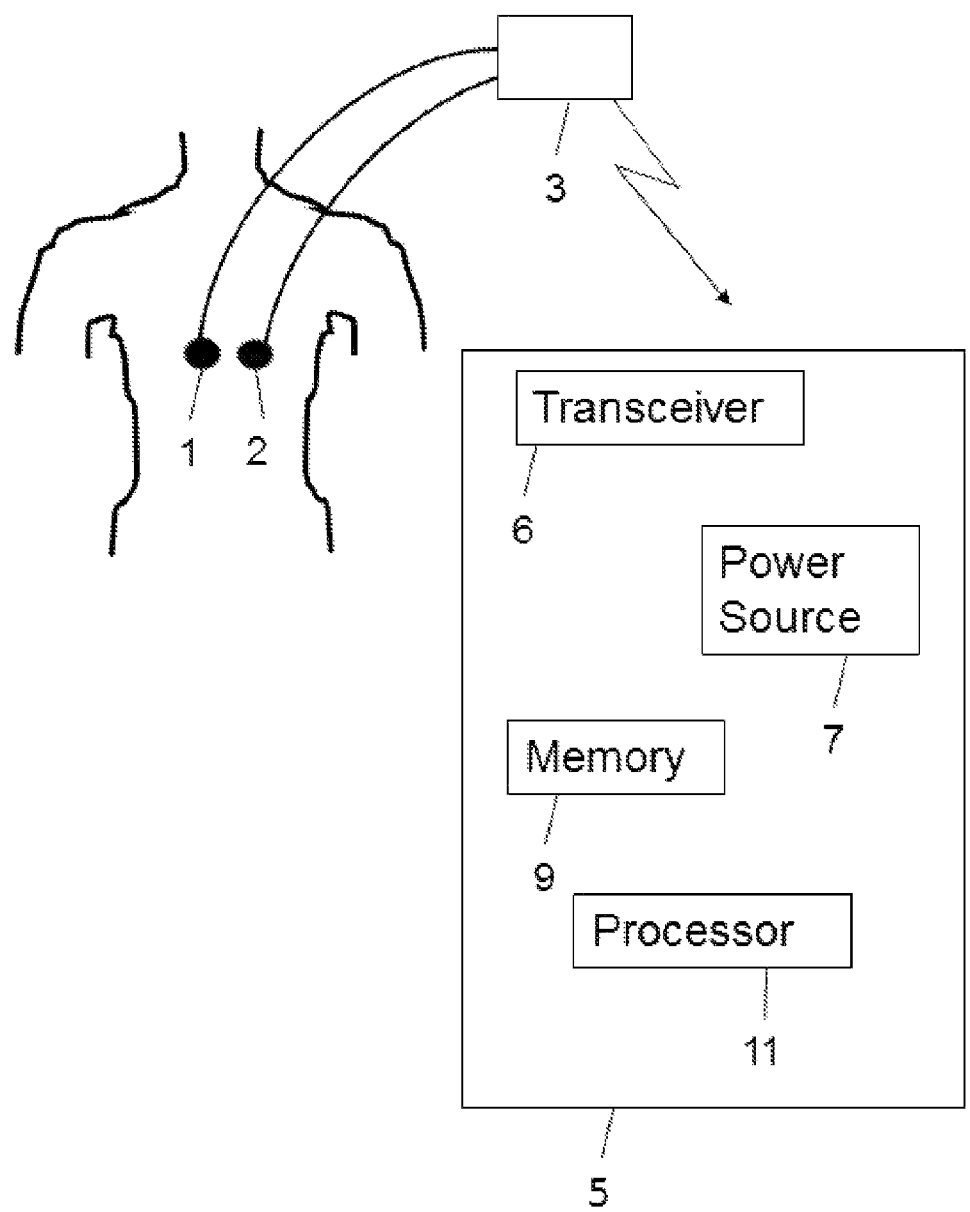
FIG. 1 shows one possible context within which the present invention may be carried out.

FIG. 1 shows one possible context within which the present invention may be carried out. A pair of sensors, electrodes 1 and 2 are disposed on the torso of a human body. The electrodes 1 and 2 are connected to a recorder 3, which records the voltage signals therebetween. The recorder 3 may implement the cardiac analysis features of the present invention, or it may wirelessly transmit the recorded signals, after varying degrees of amplification, filtering and other processing, to a monitor 5. The monitor 5 comprises a transceiver 6 that receives signals from the recorder 3. The signals are stored in a memory 9, and processed according to the methods described herein by the processor 11. A power source 7 provides energy to the monitor 5. More details on various hardware components associated with recorder 3 and processor 5 may be found in Chen et al., "Body Area Networks: A Survey," Mobile Networks and Applications, April 2011, Volume 16, Issue 2, pp 171-193, which is incorporated by reference herein. In no way is the present invention limited to body area networks.

Figure 2:
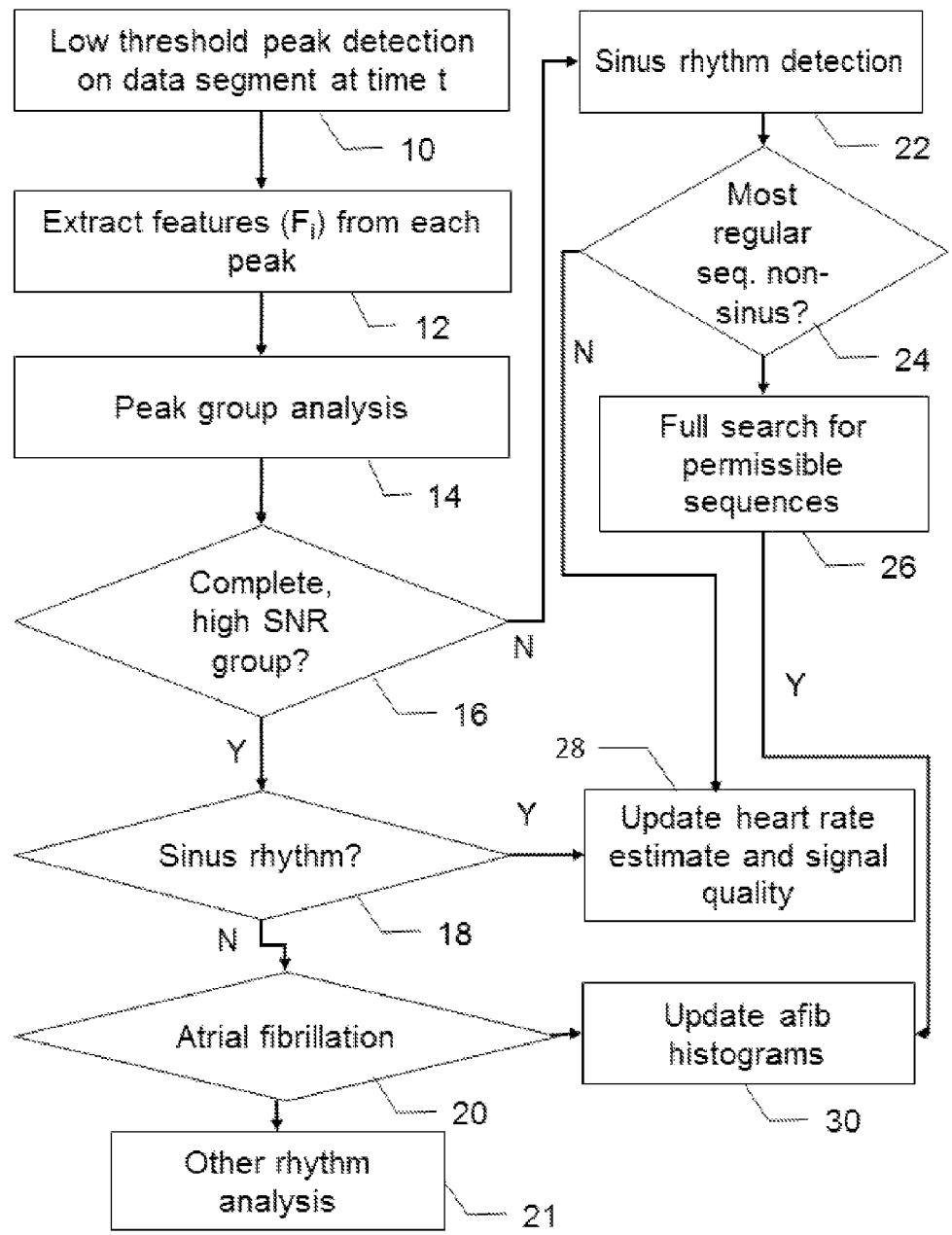
FIG. 2 is a high level flow chart of a heart beat detection and rhythm detection method according to the present invention.

FIG. 2 is a high level flow chart of a heart beat detection and rhythm detection method according to the present invention. The processing starts with a cardiac signal that has been acquired and suitably processed by, for example, a system such as that shown in FIG. 1. In block 10, low threshold peak detection is performed on a current data segment. Peak detection is preferably performed after converting the analog cardiac signal to digital form but it is possible to perform analog peak detection and: 1) thereafter convert the signal to digital and then segment the signal; or 2) segment information (e.g. peak times and amplitudes) derived from the analog signal.

An exemplary data segment duration (T) is 10 s. Peak thresholds are set so that any peak that is not clearly at the noise level is detected; since, as will be described below, the top N "best" peaks are selected for further processing, the exact detection threshold does not matter as long as it is set sufficiently low to capture any peak this is possibly a true one. The peak times are unconstrained except that peaks within 50 ms of one another are preferably merged and the average peak time of the two peaks is used for the merged peak.

In block 12, features P, are extracted from each detected peak. $F_1$ is the maximum value of the absolute value of the slope of the peak. $F_2$ is the external value of the first peak deflection, $F_3$ is the external value of the second peak deflection, $F_3$ is the external value of the third peak deflection, $F_4$ is the time between $F_2$ and $F_3$, and $F_5$ is the time between $F_3$ and $F_4$. (If a positive peak is followed by a negative peak, or vice versa, so that the two share an external point, the two peaks are merged.)

In block 14, a peak group analysis is performed. The features $F_1$ are processed by statistical and clustering routines to determine if there is a group of peaks that is separable from the remaining peaks. This will be further described with reference to FIG. 3. It there is a group of peaks that is separable, then block 16 transfers control to block 18, which analyzes the rhythm associated with the chosen group of peaks. Otherwise, block 16 transfers control to block 22, which performs a sinus rhythm search, as will be described with reference to FIGS. 3-12.

Block 18 determines whether the selected group of peaks corresponds to sinus rhythm. The sinus rhythm quality check performed in block 24 may be utilized to make this determination. Alternatively, a variety of publicly known techniques may be used to make this determination. If sinus rhythm is detected, block 18 transfers control to block 28, which updates the heart rate estimate and signal quality measures utilized by the sinus rhythm routine, as will be further described with reference to FIGS. 3-12.

If sinus rhythm is not detected, block 18 transfers control to block 20, which checks whether the selected group of peaks is characterized by atrial fibrillation. If so, block 20 transfers control to block 30, which updates atrial fibrillation histograms, which will be further described with reference to FIG. 13. Otherwise, block 20 transfers control to block 21, which performs a general rhythm analysis (e.g. bigeminy, tachycardia.)

Returning to block 22, a sinus rhythm detection routine is performed, as will be further described with reference to FIG. 4 and associated figures. If the most regular sequence can be classified as sinus rhythm (block 603 of FIG. 9), then block 24 transfers control to block 28. Otherwise, control transfers to block 26, which performs a full sequence search for permissible (i.e. physiologically possible) sequences. The best sequence is selected, as will be further described with reference to FIG. 13, and the atrial fibrillation histograms are updated in block 30.

Figure 3:
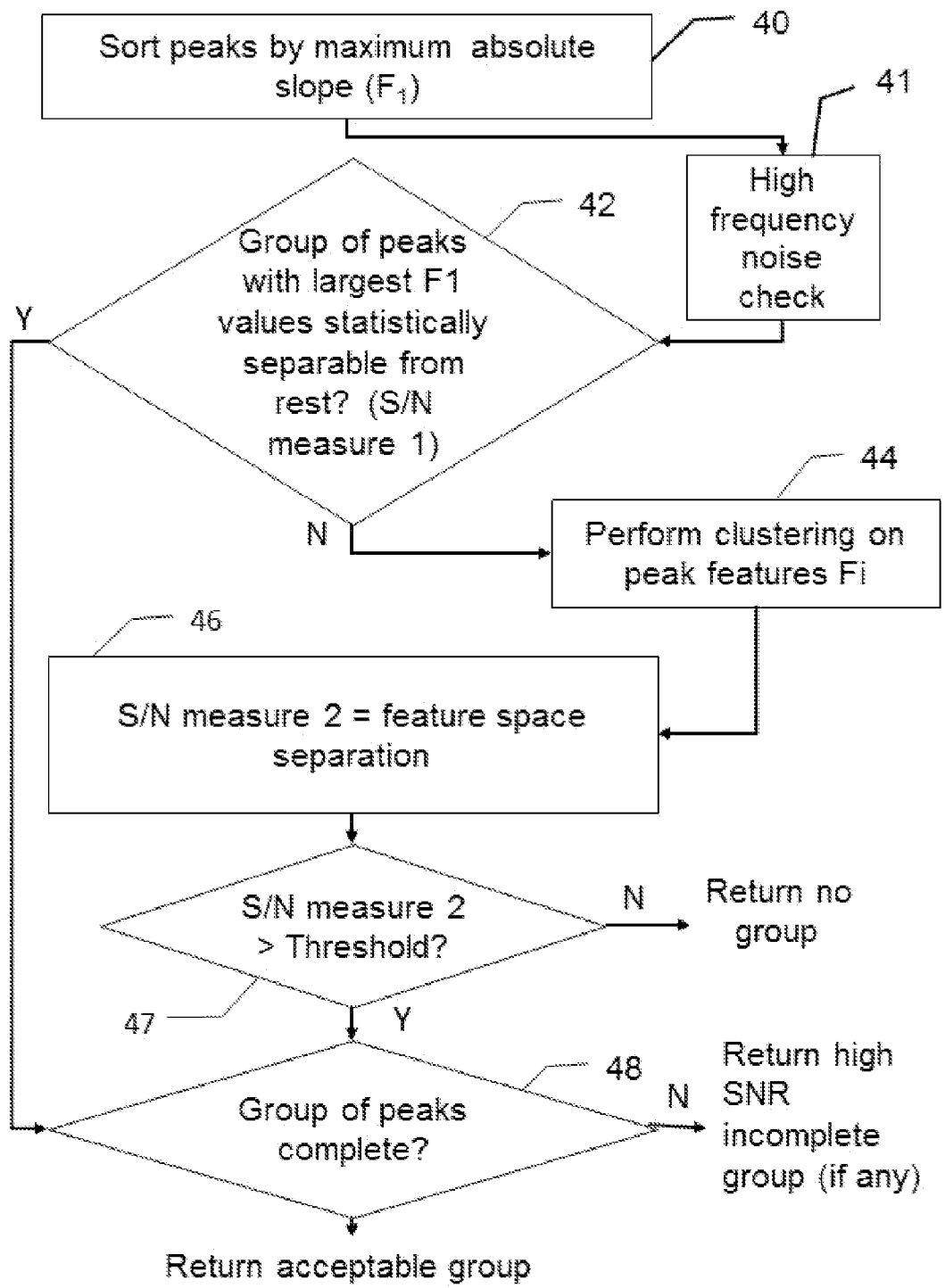
FIG. 3 is a flow chart of a routine that groups peaks according to shape characteristics.

FIG. 3 is a flow chart of a routine that groups peaks according to shape characteristics and which determines whether a group of peaks can be separated from noise. Blocks 40 and 42 perform one test for determining whether a group of peaks is separable from noise. In block 40, the peaks are sorted by their maximum absolute slope, which is feature $F_1$. Next, block 41 performs a high frequency noise analysis by checking whether a large number of large (i.e. high $F_1$ values) peaks with similar $F_1$ values occur within a short time interval. If so, a high frequency noise source (e.g. electromyogram) is a likely cause, and all of the peaks within the interval are excluded from further analysis (even though one of them may correspond to a heartbeat).

Next, block 42 determines whether the largest (in $F_1$) peaks are, with a high degree of likelihood, different than the remaining peaks. This test is performed by computing the difference ($\Delta F_1$) in $F_1$ values between adjacent (sorted) peaks. In a randomly selected sample of Nr objects with a feature space value that spans a range R, the chance that a gap in R will exceed $\Delta F_1$ can be calculated in closed form. If this probability is very low for the maximum value of $\Delta F_1$, then the signal-to-noise ratio will tend to be high, and block 42 transfers control to block 48, which checks for the completeness of the group, as will be further described below. Otherwise, block 42 transfers control to block 44.

Block 48 determines whether the group of separable peaks is complete as follows. First, the number of peaks must exceed a threshold. For example, if the segment length is 10 seconds, there must be at least 5 beats (assuming e.g. a minimum heart rate of 50 bpm). It so, then the RR intervals are computed and the number of RR intervals within 300 ms of one another (Nrr) is determined. The mean RR interval of the peaks within this group (RRg) is determined, and the number of implied RR intervals Irr=T/RRg is determined. If Nrr>0.7*Irr, then the group of peaks is considered complete. If not, the group of peaks is considered complete only if there are no more than two RR intervals (meaning the time between adjacent peaks, even if not a true RR interval) more than 1200 ms long. Otherwise, the group is incomplete, and the high SNR but incomplete group is returned.

Figure 16:
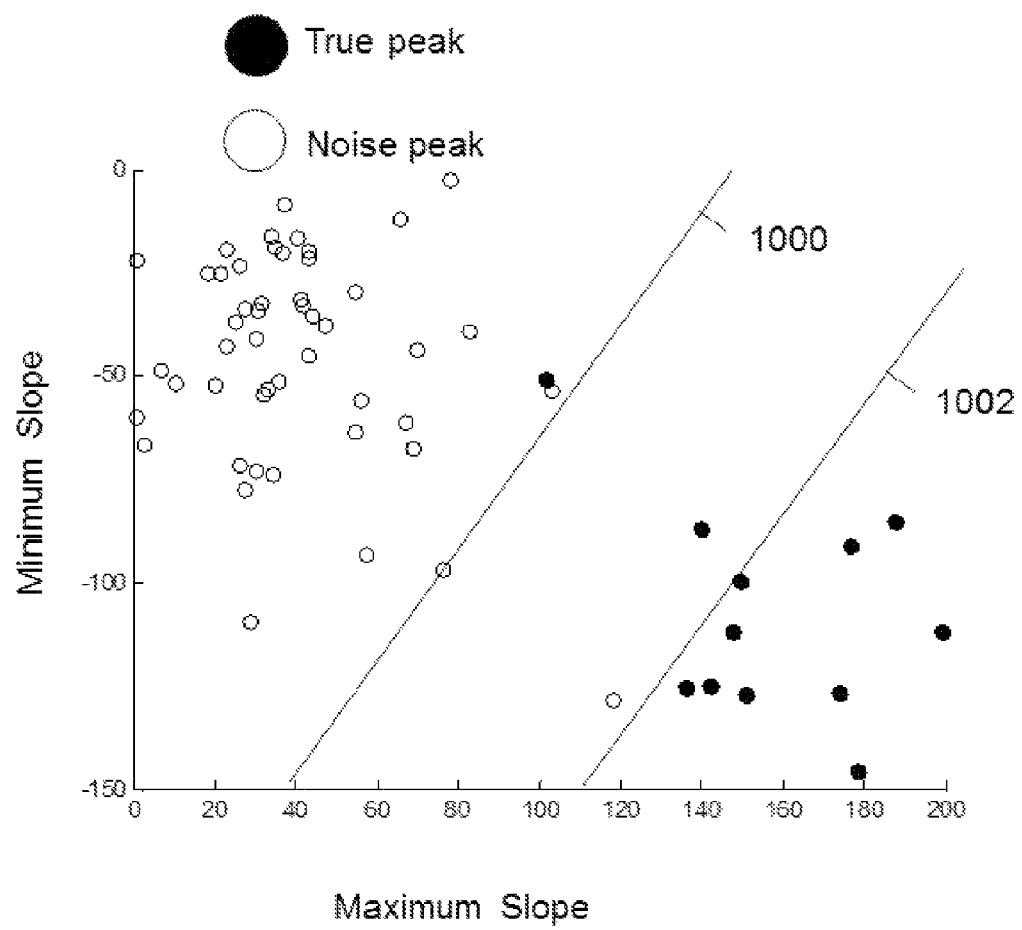
FIG. 16 shows a plots of the maximum and minimum slopes of true peaks and noise peaks, along with lines that show a measure of feature space separation.

Returning to block 44, clustering such as that shown in FIG. 16 or (e.g. OPTICS) is performed on the features $F_1$. In block 46, the likelihood (S/N measure 2) of the best group/cluster is assessed by computing a measure of feature space separation, as will be further described with reference to FIG. 16. An alternate measure of signal to noise is: (group feature space hypervolume/total feature space hypervolume)$^{Ng}$, where Ng is the number of elements in the group. The total feature space hypervolume is based on the range of possible values for each feature.

There are known methods for calculating spherical hypervolumes. A computationally simpler approach is to calculate parallelepiped based hypervolumes. For example, if there are only two features in the feature space, the hypervolume collapses to an area, $\Delta F_{1,g}*\Delta F_{2,g}$, where $\Delta F_{1,g}$ is the maximum value of $F_1$ in the group minus the minimum value of $F_1$ in the group and likewise for $\Delta F_{2,g}$. The total feature space hypervolume is $\Delta F_1*\Delta F_2$, where $\Delta F_1$ is the maximum value of $F_1$ in the across all peaks minus the minimum value of $F_1$ across all peaks and likewise for $\Delta F_2$. Alternatively, if the external values of the features are known a priori, these may be used instead of the external values of the existing peaks to calculate total feature space hypervolume.

A bigeminal rhythm may be characterized by two separate clusters, in which case the above likelihood test is altered so that the individual likelihoods of the clusters are multiplied together. More generally, if there are a plurality of clusters, the likelihood test involves multiplication of the individual cluster likelihoods.

Block 47 determines whether S/N measure 2 exceeds a threshold. If so, then control transfers to block 48 for a completeness check. Otherwise, the routine returns the result that there are no high S/N groups.

Figure 4:
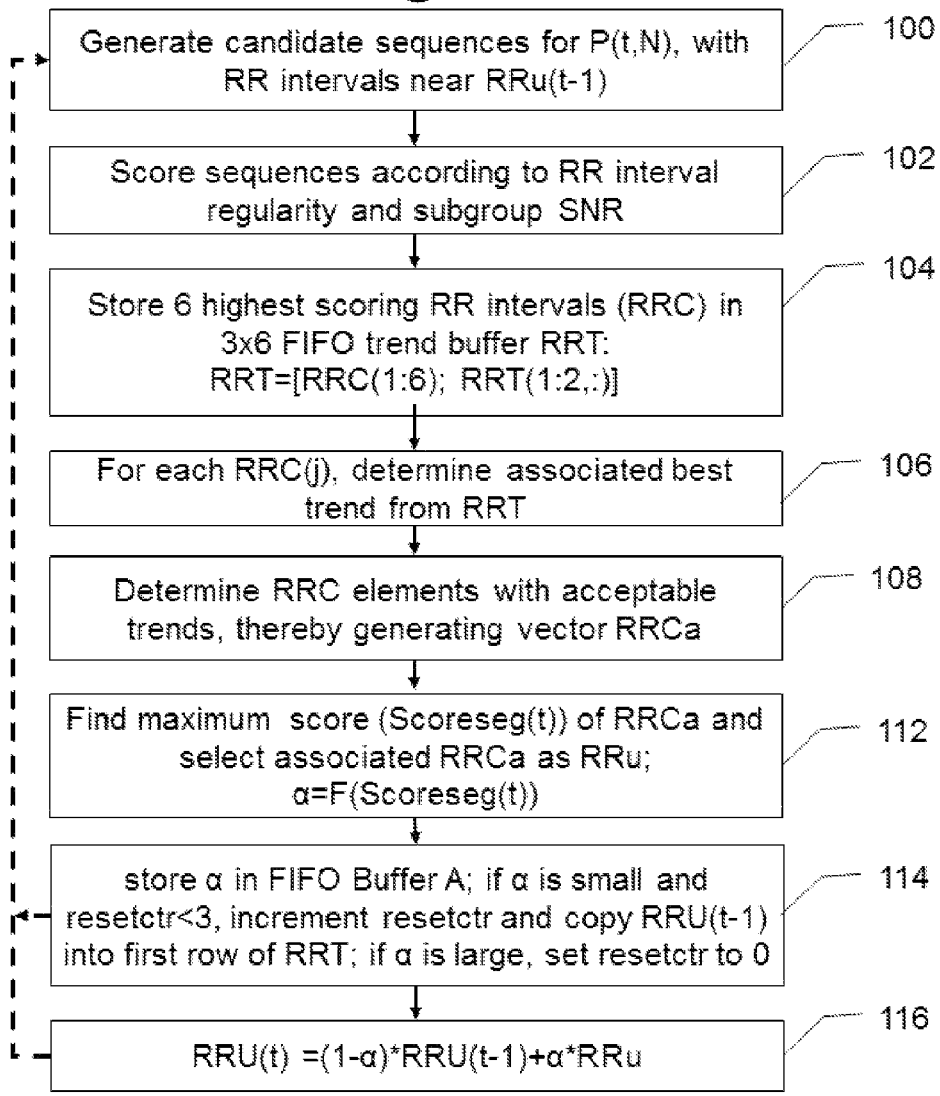
FIG. 4 is a high level flowchart of a sinus rhythm detection routine that is further specified in FIGS. 5-12.

FIG. 4 is a high level flowchart of the sinus rhythm detection routine invoked by block 22 of FIG. 2. The cardiac signal data incoming to the routine in FIG. 4 has been segmented such that there exists an ordered set of peak time vectors P(t,1:N), where N is the number of peaks in the data segment at time t. (The peaks were detected in block 10 of FIG. 2.) Further, the peak group analysis (FIG. 3) has selected the N "best" peaks from each set of peaks in a segment based on maximum absolute slope criteria, if there was no high SNR group. If there was a high SNR group with Ng (<N) members, then the N peaks comprise these Ng members along with the N−Ng peaks that have the largest maximum absolute slopes (and that are not one of the Ng high SNR group members.) For example, if segments are 10 seconds long, N may be 25.

In block 100, candidate beat sequences are generated from P(t,1:N), as will be further described with reference to FIG. 5a (in the case where there are no high SNR groups) and 5b (in the case where there is a high SNR group. The candidate sequences are within an RR interval range that is a function of the current filter output RR interval (RRu(t−1)), and the quality of recent sequences that resulted in RRu(t−1), as indicated by the dashed feedback lines from blocks 116 and 114, respectively. The RR interval range is a function of the recent sequence quality: if recent sequence quality is high, then the range is the minimum physiologically reasonable value, whereas if recent sequence quality is very low, then the range requirement is removed entirely. Recent sequence quality is stored in the FIFO vector A (block 114). According to one embodiment, recent sequence quality is an average of the last few a values stored in A, where a is a measure of the current sequence quality, as will be further described with reference to block 112. The RR interval range constraint will be further described with reference to block 204 (FIG. 5).

In block 102, the sequences are scored according to their RR interval regularity and subgroup SNR, as will be further described with reference to FIG. 9. In block 104, the RR intervals associated with the best (highest scored) 6 sequences, which will be referred to as $RR_x$ (where x is an integer from 1 to 6), are stored in a FIFO trend buffer, RRT. The first two rows in RRT are shifted down a row such that the last (oldest) row in RRT is removed.

In block 106, the best trend associated with each element $RR_x$ is determined. The best trend is the path through RRT that results in the smallest second difference: as shown in block 900 of FIG. 12, for each of the candidate RR intervals in the current segment (time t), i.e. $RR_x(t)$, the path through the prior two sets of segment RR intervals is found that minimizes the second derivative (more formally, second finite difference), i.e., for $RR_x(t)$, the values of y and z are found that minimize $RR_x(t)''=|RR_x(t)-2*RR_y(t-1)+RR_z(t-2)|$, subject to each difference being less than a threshold T1. Specifically, it is required that $|RR_x(t)-RR_y(t-1)|<T1$ and $|RR_y(t-1)-RR_y(t-2)|<T1$. T1 is a physiological constraint and may be determined from a priori population RR interval data and/or from subject specific information. If segments are 10 second long and consecutive, a reasonable value for T1 is 20 beats/minute. If $RR_x(t)''$ is less than a threshold T2, then $RR_x$ remains a candidate RR interval; the remaining such $RR_x$'s form vector RRCa. T2 may be determined in a manner similar to that of T1.

Figure 10:
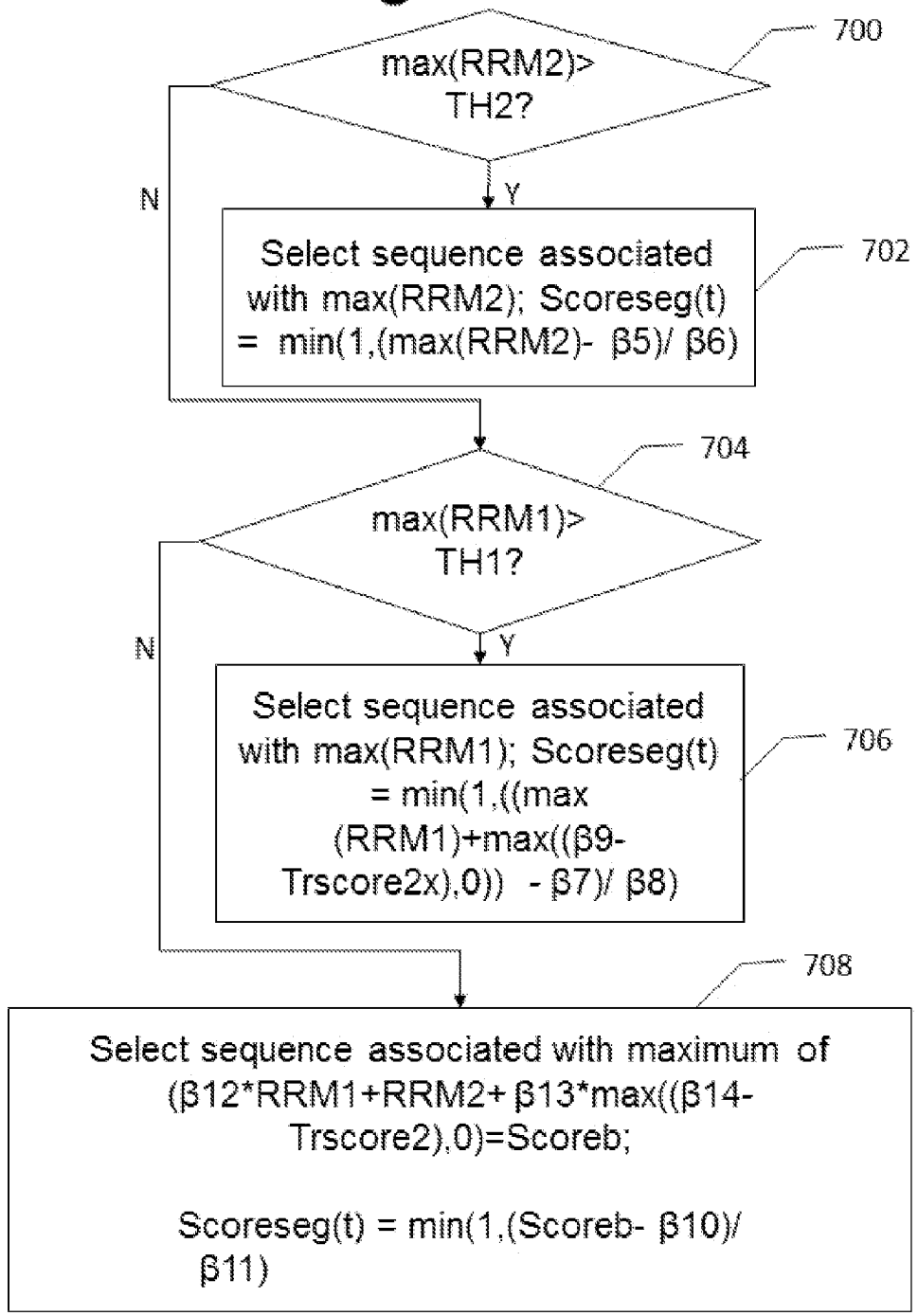
FIG. 10 shows the steps associated with selecting the best sequence and associated RR interval value.

Two trend scores, Trscore1 and Trscore2, are calculated for each of the sequences associated with the RRCa $RR_x$'s, as show in blocks 902 and 904 respectively of FIG. 10. Larger values of Trscore1 and Trscore2 are penalized, as will be described below. Trscore1 is related to the second derivative calculated in block 900, and Trscore2 is the difference between a current RR interval candidate $RR_x(t)$ and the last RR estimate RRu(t−1).

In block 112, the maximum RR regularity score (Scoreseg(t)) over RRCa is determined as will be described with reference to FIGS. 9 and 10, and the associated RRCa is selected as the final RR interval (RRu) for the segment. The weight, α, to be accorded RRu in the update step (block 116) is a function of this score: $RRu(t-1)=(1-\alpha)*RRu(t-1)+\alpha*RRb(t)$, where $\alpha=\alpha 0+(1-\alpha 0)*Scoreseg(t)$. (The relationship between a and Scoreseg(t) may be determined by performing optimization with known RR interval data corrupted with noise, as will be further described herein.) In block 114, α is stored in FIFO vector A. In block 116, the RR interval output is updated according to an exponential average based on α. In an alternative embodiment, the current trend is added to the previous filter output (RRu(t−1)) in the exponential average.

Figure 5:
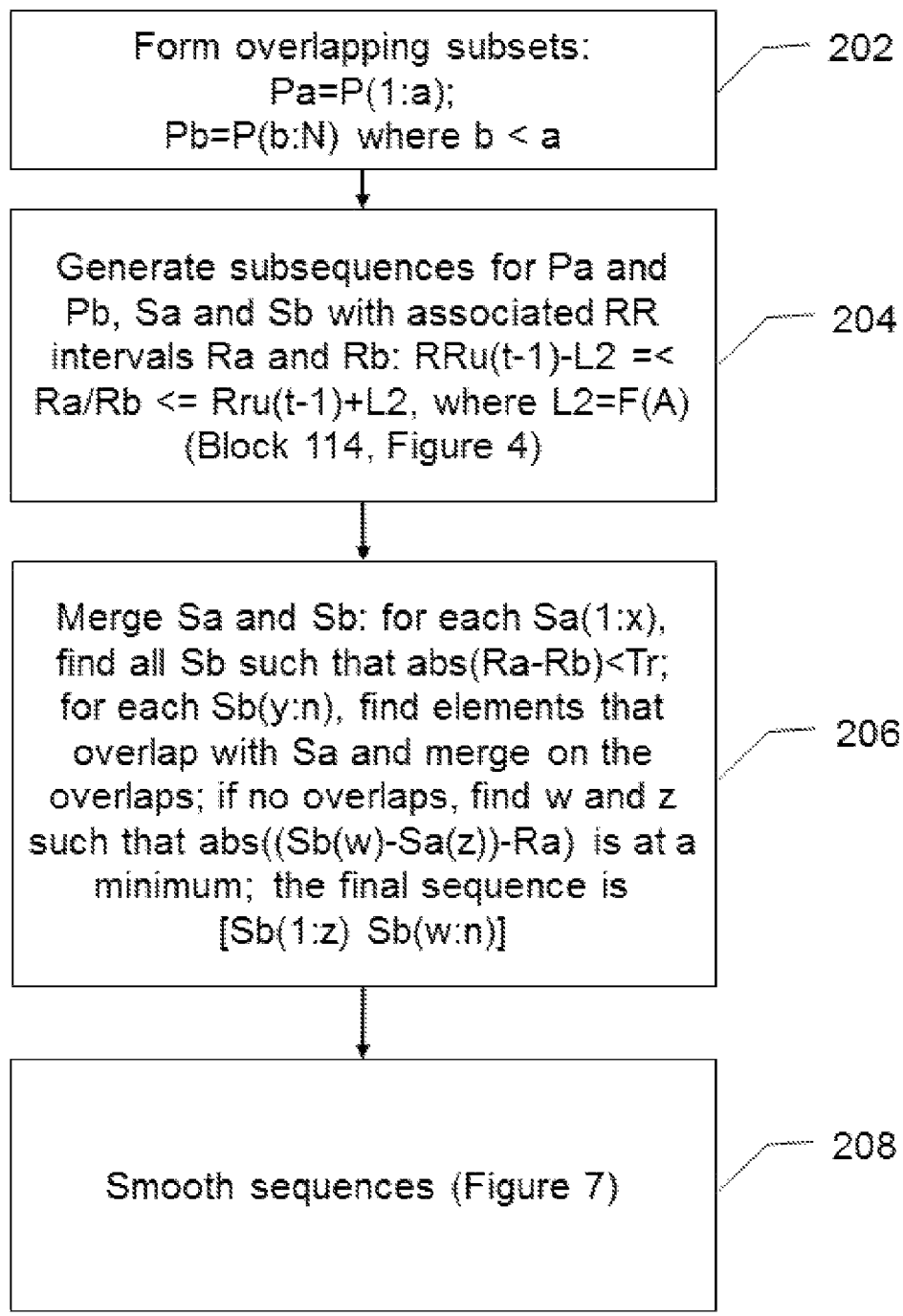
FIG. 5 is a flowchart for a routine that generates candidate sequences from peak times within a data segment.

FIG. 5 is a flowchart for a routine that generates candidate sequences from peak times within a data segment in the case where there are no high SNR (but incomplete groups). In step 202, the peak times within P(t,N) are divided into two overlapping sets. The overlap is preferably chosen according to the number of peaks. For example, if N=25, Pa may be set as P(1:16) while Pb may be set as P(10:25). Alternatively, the area of overlap may be chosen based on the timing of the peaks.

In step 204, candidate sets of subsequences Sa and Sb are generated for both Pa and Pb, as will be further described with reference to FIG. 6. Each subsequence is characterized by an associated RR interval: RRa represents the set of RR intervals associated with Sa while RRb represents the set of RR intervals associated with Sb. RRa and RRb are selected such that they are within L2 mms of RRu(t−1), where L2 is a function of recent signal quality stored in vector A (Block 114, FIG. 4). If recent signal quality is high, then L2 is preferably on the order of 150 ms, whereas if recent signal quality is very low, L2 is sufficiently large that the RR proximity constraint is effectively removed. L2 may take on intermediate values for intermediate signal qualities. As mentioned, F(A) is preferably an average of the last few signal quality values Scoreseg (t).

In step 206, the subsequences from the two sets Sa and Sb with relatively close RR intervals are merged with one another such that the overall RR interval sequence is smooth. If there is an element in common between two sequences, it serves as the merge element, so that the merged sequence comprises: (i) the first sequence up to the common element; (ii) the common element; and (iii) the second sequence after the common element. If there is no element in common between two sequences, each element in the first sequence is separately examined: the second sequence is searched to find the element that forms the best match with the first sequence element, where best match means the resulting RR interval between the first sequence and second sequence elements is closest to the desired RR interval, which is the RR interval associated with the first sequence (or alternatively, the average RR interval associated with the first and second sequences.) The best match over all of this set of best matches is then selected. For example, if Sa=[0 500] and Sb=[400 1000 1500], and the RR interval associated with Sa is 500, then 1000 is chosen as the Sb element since 1000−500 (=500) is closer to the desired RR interval (500) than the RR interval associated with the best match for Sa=0, which is Sb=400, with a resulting RR interval of 400. Note that if no RR interval is within a specified threshold of the desired RR interval, then the best match is defined as the RR interval that minimizes the modulus relative to the desired RR interval. For example, if Sa=[0 500] and Sb=[1600 2010 2560], and as before the desired RR interval is 500, then 2010 is chosen as the best match for 500, since mod(2010−500,500)=10, which is smaller than mod(1600−500,500)=100. (Note that 0 and 2010 also match with the same minimum modulus of 10. In the case of multiple matches, the largest element in Sa, in this case 500, is chosen.)

Figure 7:
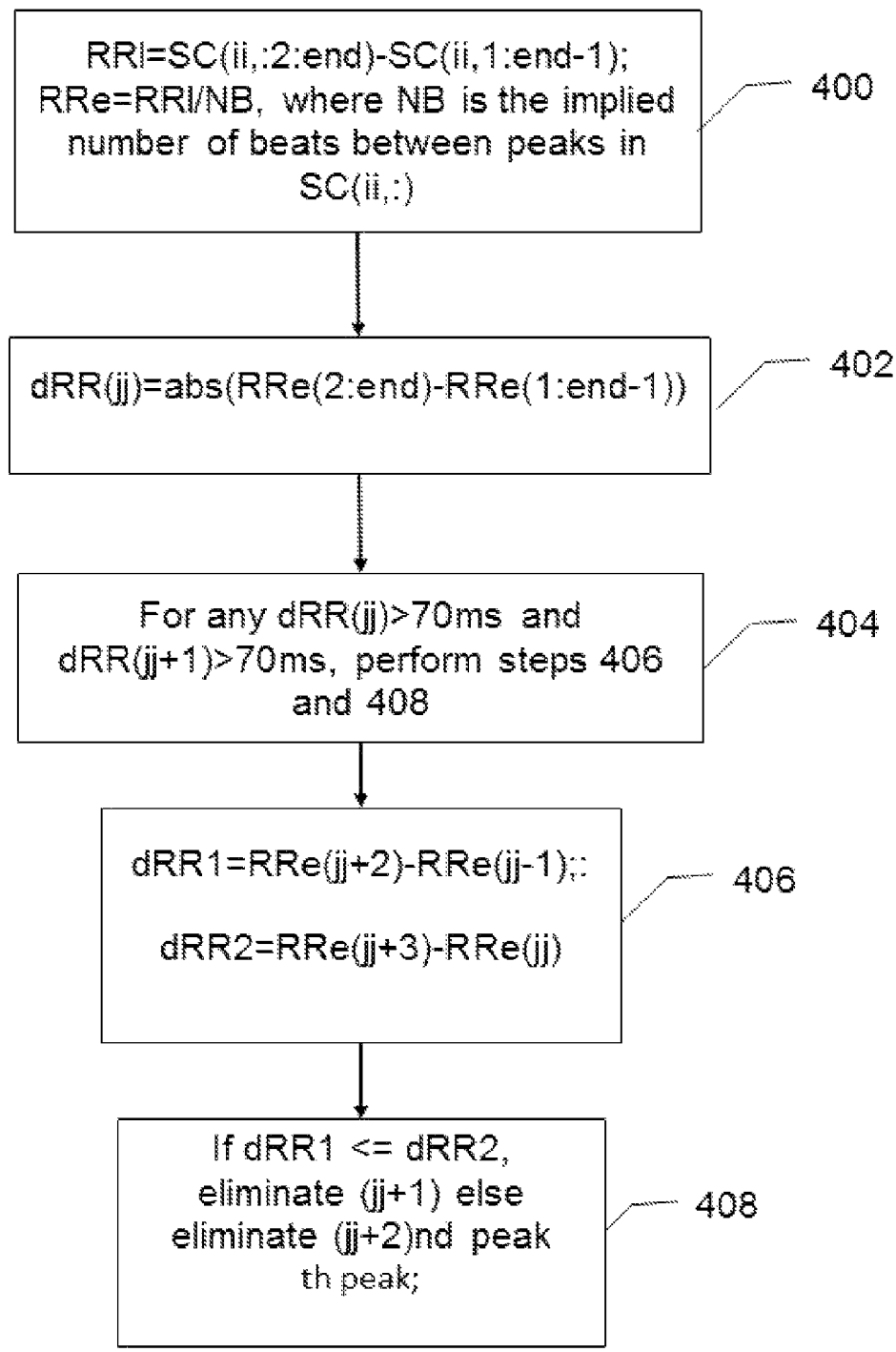
FIG. 7 is a flowchart of a procedure that eliminates outlier peaks from sequences to decrease overall RR interval variability.

In step 208, the sequences are smoothed by removing unwanted RR intervals, as will be further described with reference to FIG. 7. In an alternate embodiment, a number of baseline/partner pairs may be selected from the middle of P, and Sa works back from the middle while Sb works forward from the middle. This avoids the need for a merger step, since Sa and Sb are created from a baseline/partner pair in common.

Figure 6:
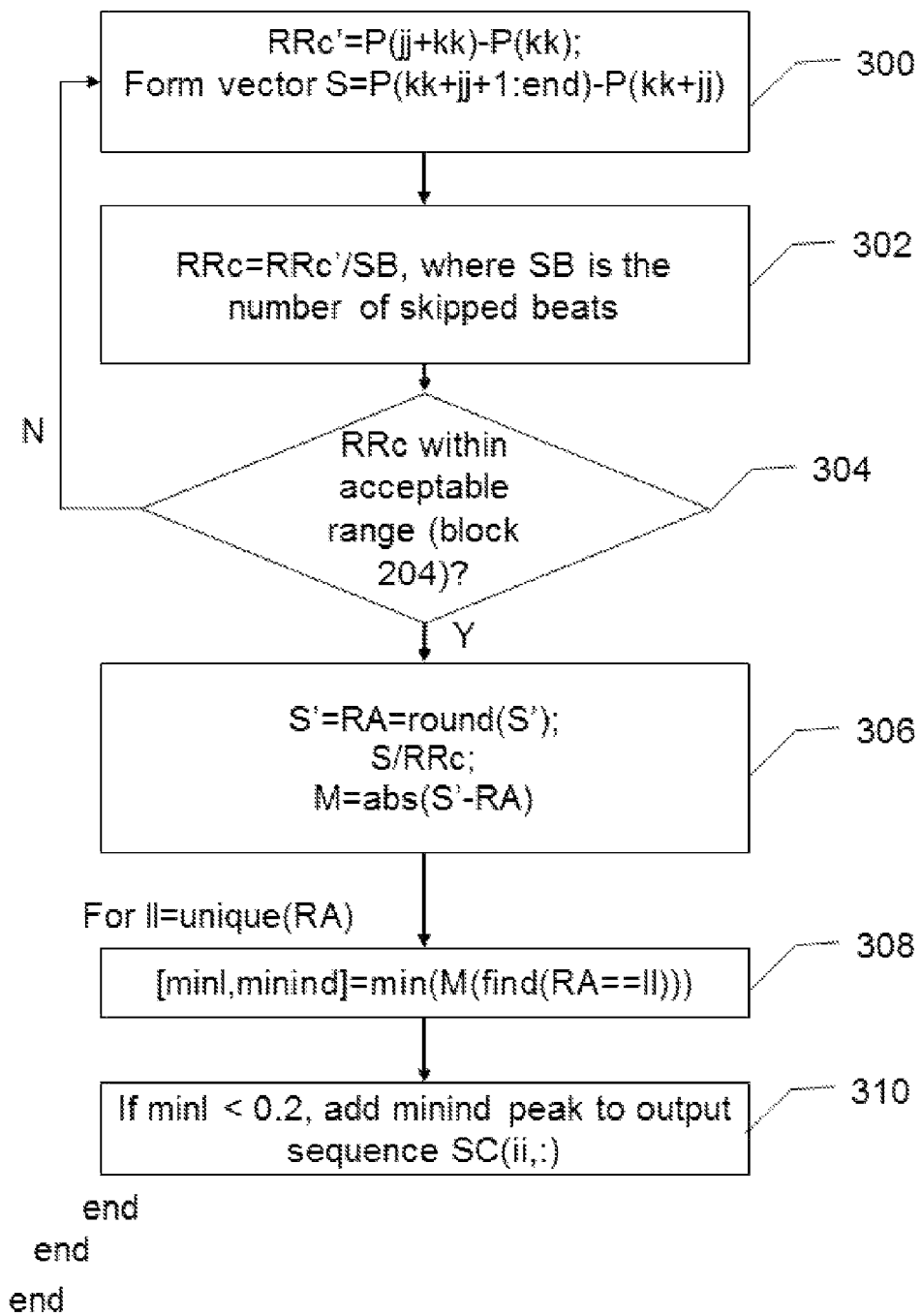
FIG. 6 is a flowchart of a subsequence generating procedure called by the sequence generating procedure associated with FIG. 5.

In the case where there is a high SNR group of peaks, the FIG. 6 sequence generating routine is performed with the constraint that all group members must be within a sequence.

FIG. 6 is a flowchart of the subsequence generating procedure. Possible RR intervals are effectively sampled by computing the times between a number of peak combinations. For example, if there are 10 peaks in peak set P, then the first 3 peaks may be selected as possible "baseline" peaks; for each of these three peaks, a number (e.g. 3) of the closest following peaks may be chosen as potential partners for the baseline peak. In this example, there are nine possible RR intervals (less redundant RR intervals). In the flowchart, sequences are generated by looping over the baseline peak counter, na, and the possible partner counter, nb. (In the above example, na and nb are both 3.)

For a particular baseline/partner pair, in block 300, a provisional RR interval RRc' is set equal to the time between the baseline peak and its partner. A set S is formed from the remaining peaks by subtracting the time of the partner peak (P(kk+jj)), thereby referencing all of the remaining peaks to the partner peak. This referencing will enable the use of a division (modulo) scheme to locate peaks associated with RR intervals close to the initial RR interval (RRc), as will be further described below.

Because baseline/partner pairs may correspond to the true sequence yet have beats missing therebetween, the possible number of missing beats SB (if any) between the baseline/partner pair is determined according to a routine described with reference to FIG. 8. As an example, assume that the true sequence is [1 501 1001 1501 2001] but that beat 501 does not exist in P due to noise, so that P is [1 1001 1501 and 2001]. If the baseline/partner pair under consideration is [1 1001], then the effective RR interval RRc is 500, ½ of the time between the baseline partner pair. Block 302 calculates the effective RRc according to the number of skipped beats determined by the skipped beat routine (FIG. 5).

Block 304 determines whether RRc is within the acceptable range established in block 204 (FIG. 5). If not, the process returns to block 300 to fetch the next baseline/partner pair. If the RRc is acceptable, in block 306, S is normalized to RRc', to form normalized vector S'. The nearest integer for each member of S' is determined to form vector RA, and the remainder quantity vector M=abs(S'−RA) is computed.

Blocks 308 and 310 are performed for each unique integer value in the set RA. For each such integer, the peak that is closest to being on the "grid" corresponding to RRc and the baseline/partner pair is determined by finding the smallest M for that integer. For example, if RA=[2 2 3] and the corresponding M vector is [0.3 0.15 0.05], when the "grid" integer is 2, the peak associated with 0.15 is selected (because 0.15 is less than the other candidate, 0.3). The selected peak is added to the output sequence SC(ii,:) only if its M value is less than 0.2. The FIG. 6 routine outputs an array of sequences, SC, where each row in SC is a single sequence.

Sequences resulting from the previously mentioned search procedure may contain unwanted peaks, i.e., the sequence regularity scores would be increased with the removal of certain peaks associated with relatively large changes in RR interval. FIG. 7 is a flowchart of a procedure that eliminates such unwanted peaks. In block 400, the effective RR intervals, RRe, are calculated for a sequence S(ii,:) by dividing the raw RR interval by the implied number of beats between the peaks. (For example, if the overall RR interval associated with S(i,:) is 700 ms and the raw RR interval between adjacent peaks is 1430 ms, then the effective RR interval associated with those peaks is 715 ms.) In block 402, the first change in RRe is computed, thereby generating change measure dRR. In block 404, the routine searches for consecutive dRR's that each exceed 70 ms, indicating that some peak is causing abrupt shifts in RR interval. The bad peak may occur at either of two locations; blocks 406 and 408 determine which peak to eliminate.

Specifically, block 406 computes change in RR interval measures associated with the removal of the (jj+1)st peak and (jj+2)nd peak, respectively. Block 408 checks whether the removal of the (jj+1)st peak results in a smaller change in RR interval than the removal of the (jj+2)nd peak, and the appropriate peak is removed accordingly.

Figure 8:
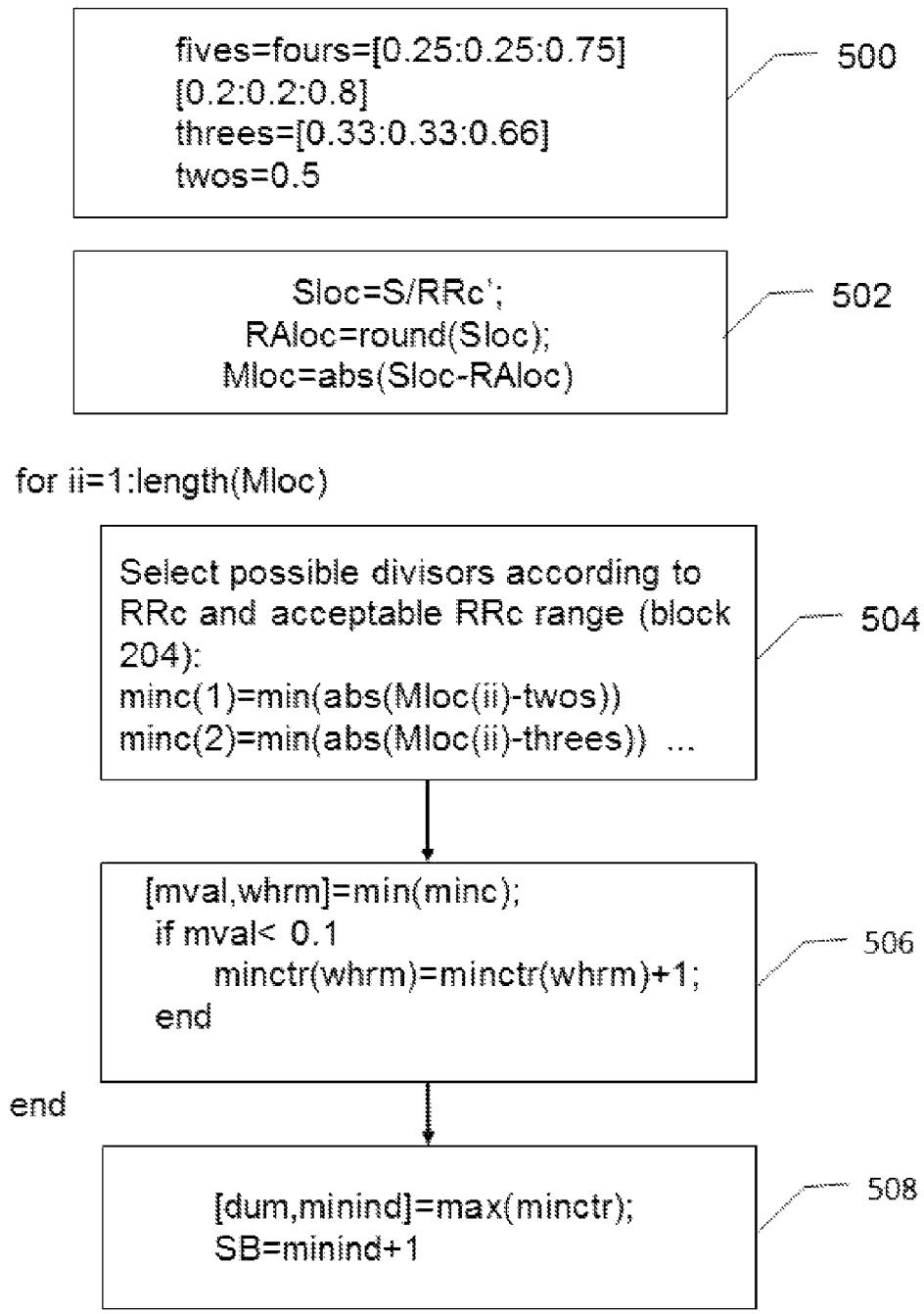
FIG. 8 is a routine that determines the number of skipped beats between baseline/partner pairs.

FIG. 8 is a routine that determines the number of skipped beats between baseline/partner pairs. The possible number of skipped beats is a function of the acceptable RR range determined in block 204 (FIG. 5). For example, if the RRC' associated with a baseline/partner pair is 3000 ms, and the acceptable RR range is between 740 ms and 1010 ms, then the only possible numbers of skipped beats are 3 (RR interval=3000 ms/3=1000 ms) and 4 (RR interval=3000 ms/4=750 ms). As will be further described below, block 502 enforces the selection of possible divisors.

In block 500, a remainder vector is associated with each divisor. Continuing with a previous example, assume that the true sequence is [1 501 1001 1501 2001] but that beat 501 does not exist in P due to noise, so that P is [1 1001 1501 and 2001]. If the baseline/partner pair under consideration is [1 1001], then the desired number of skipped beats is 2 (1000/2=500, the correct RR interval). S here is [500 1000](=[1501 2001]−1001); when S is divided by RRc' (1000), the result is [0.5 1]. Generally, if 2 is the correct SB, then there will be a relatively large number of values in S/RRc' close to 0.5, while if 3 is the correct SB, then there will be a relatively large number of values in S/RRc' close to 0.33 or 0.66. The remainder vectors for each possible divisor are constructed in block 500 accordingly.

Block 502 forms the quantities mentioned in the above example: Sloc=S/RRc, RAloc=round(Sloc), and Mloc=abs(Sloc−RAloc). (The loc prefix is used to distinguish the quantities used here from the analogous quantities used in connection with the FIG. 3 routine.)

Blocks 504 and 506 loop over all Mloc elements. In block 504, the remainder vector associated with each acceptable divisor (i.e. one that corresponds to an acceptable RR interval, as previously described), is subtracted from the current Mloc entry. In block 506, the divisor associated with the smallest difference between the corresponding remainder vector and Mloc is chosen. If this difference is sufficiently small, then a counter associated with that remainder vector is incremented. In block 508, the largest counter is selected, and the number of skipped beats SB set accordingly.

Figure 9:
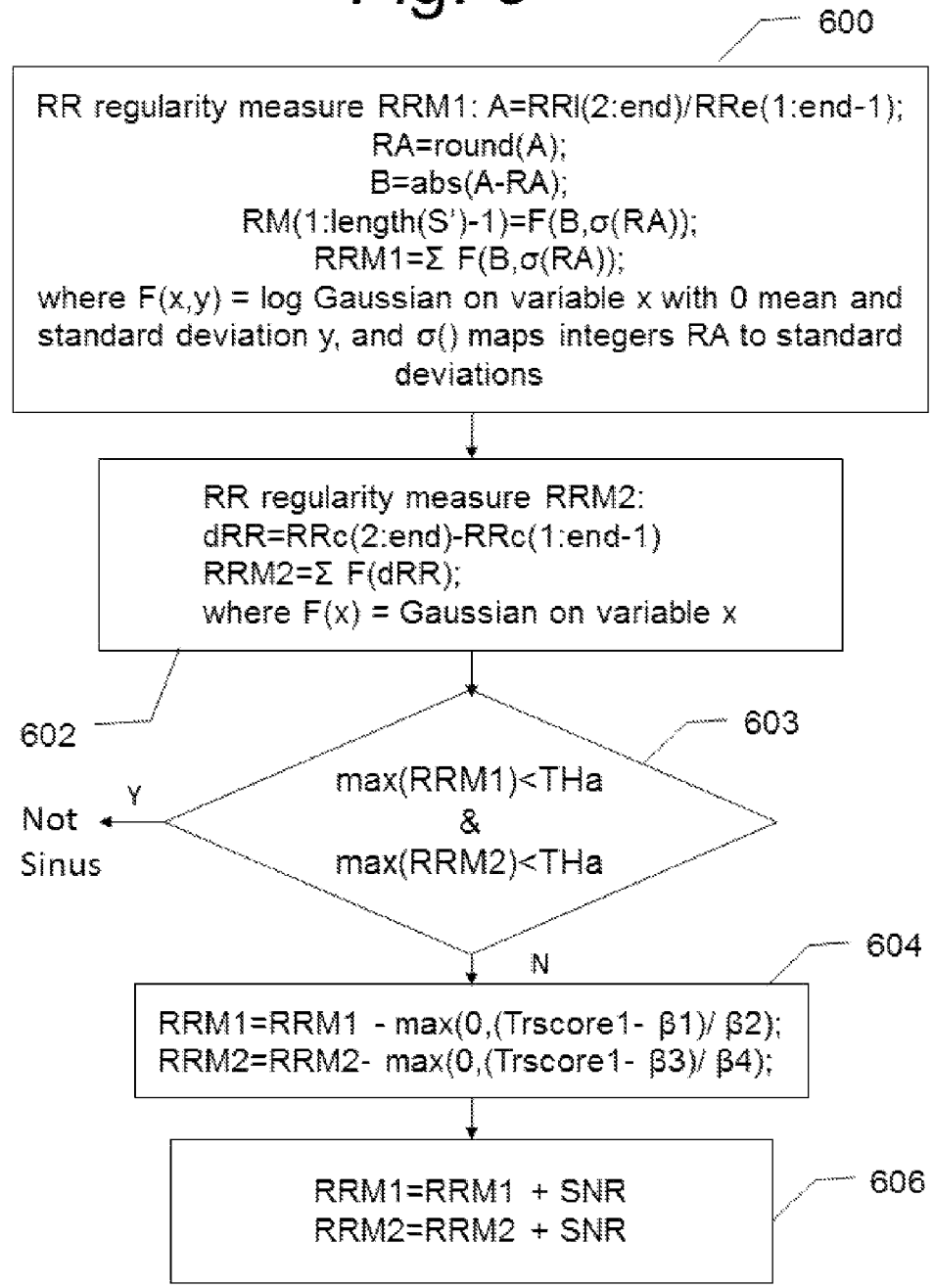
FIG. 9 is a flowchart of a routine that scores sequences according to RR interval regularity, RR interval trend, and a signal to noise ratio measure.

FIG. 9 is a flowchart of the sequence scoring routine. For each sequence, two regularity measures, RRM1 and RRM2, are calculated. Each of these measures is based on beat to beat changes in RR interval; smaller changes in RR interval lead to larger regularity scores for each of these measures. RRM1 is a log-likelihood measure that is the sum of the log likelihood for the SN−2 changes in RR interval in a sequence with SN peaks (and therefore SN−1 RR intervals). RRM1 penalizes changes in RR interval that are unlikely. RRM2 is similar to RRM1 except that it does not penalize unlikely changes in RR interval, it effectively does not take into account skipped beats, and it is not normalized by RR interval. The Gaussian distributions used for RRM1 and RRM2 may be based on the sinus rhythm statistics of normal subjects from publicly available databases (e.g. at physionet.org). Exemplary distributions for RRM1 and RRM2 are shown in plots 992 and 990, respectively, in FIG. 15.

Block 600 shows equations associated with the calculation of RRM1. The time RRI(jj) between adjacent peaks is divided by the preceding effective RR interval RRe(jj−1). (RRe is described with respect to block 400, FIG. 7). The result is subtracted from the nearest integer (RA(jj)), which represents the effective number of beats between the peaks, to generate a measure of normalized change in RR interval (B(jj)).

A priori statistics are applied, based on the number of peaks between adjacent peaks. If there are no implied between adjacent peaks, RA(jj)=1, and the correct statistics to apply are based on RRap(2:end)−RRap(1:end−1), where RRap is a known, large set of true RR intervals. If there is one implied between adjacent peaks, RA(jj)=2, and the correct statistics to apply are based on RRap(3:end)−RRap(1:end−1). And so on, for other values of implied peaks between peaks. Summarizing, the particular probability distribution (F(B,σ), where B is the random variable and a the standard deviation associated with the pertinent probability distribution) that is applied to B(jj) is indexed by RA(jj): RA(jj) selects the a (more formally, the probability distribution associated with σ) to be applied to B(jj).

Block 602 shows equations associated with the calculation of RRM2, which measures changes in RR interval only for RR intervals that are close to the overall RR interval associated with the sequence. In other words, RRM2 excludes RR intervals associated with skipped beats. RRM2 is direct function of the probability distribution does not penalize large changes in RR interval. Rather, sequences that have even a few consecutive RR intervals that are close in value will tend to have large RRM2 scores, regardless of any large RR jumps in the sequence.

In block 603, the maximum RRM1 and RRM2 scores are compared to respective thresholds. If both of these maxima are below these thresholds, then the segment can not be classified as sinus rhythm, and control transfers to block 26 of FIG. 2.

Otherwise, in block 604, the RRM1 and RRM2 scores are adjusted according to the value of the sequence's Trscore1, so that large values of the second derivative (of the RR interval) are penalized. In block 606, the RRM1 and RRM2 scores are further adjusted by the SNR scores to the extent that the sequence in question includes members of a high SNR group that were accorded a SNR score in either block 42 or 46 of FIG. 3 (SNR is the S/N measure 1 or S/N measure 2, whichever is applicable.)

Blocks 620 and 622 of FIG. 11 show the steps associated with generating lists of candidate RR intervals ranked according to RRM1 (block 620) and RRM2 (block 622). Because the sequence generating procedure described with reference to FIGS. 5 and 6 possibly results in sequences that have similar RR interval values, it is helpful to group these similar sequences, so that the ranked list of candidate RR intervals for the purposes of the trend analysis includes only RR intervals that are reasonably distinct from one another. Thus, sequences are grouped together if their KK intervals are within 50 ms of one another. If there are overlapping RR intervals, i.e. RR intervals that could be associated with different groups, they are allowed to be associated with different groups. For each group, the maximum intra-group score is taken as the score for the group.

FIG. 10 shows the steps associated with selecting the best sequence and associated RR interval value. Block 700 finds the maximum RRM2 value over all sequences and compares it with a threshold. If the maximum value exceeds the threshold, in block 702 the routine selects the RR interval associated with the sequence corresponding to the maximum value and calculates the quality score for the segment, Scoreseg(t), based on a linear function of RRM2. Otherwise, control passes to block 704. The threshold may be determined based on a priori data by adding spurious peaks to a large number of RR intervals, segmenting the resulting data by randomly selecting a certain number of peaks per segment (which will therefore include a mixture of true peaks and noise peaks), and plotting the RRM2 values of a large number of sequences against a measure of quality of those sequences, defined as the percentage of true peaks in the sequence divided by the total number of true peaks in set P (block 200). There may be an RRM2 value above which the minimum quality value associated with an RRM2 value is a roughly linear relationship; this critical RRM2 value is preferably chosen as the threshold used in block 700.

Blocks 704 and 706 parallel blocks 700 and 702, with RRM1 replacing RRM2. In block 706, the quality score Scoreseg(t) is based on a linear function of RRM1 and the trend score Trscore2. If the maximum value of RRM2 does not exceed the threshold, then control passes to block 708, which forms a weighted sum of RRM1, RRM2 and Trscore2 for each sequence, and selects the sequence associated with the largest sum. The weights may be determined by an optimization routine that compares filter output (block 116) with known values. Scoreseg(t) is also computed according to the aforementioned weighted sum of RRM1, RRM2 and Trscore2.

Figure 13:
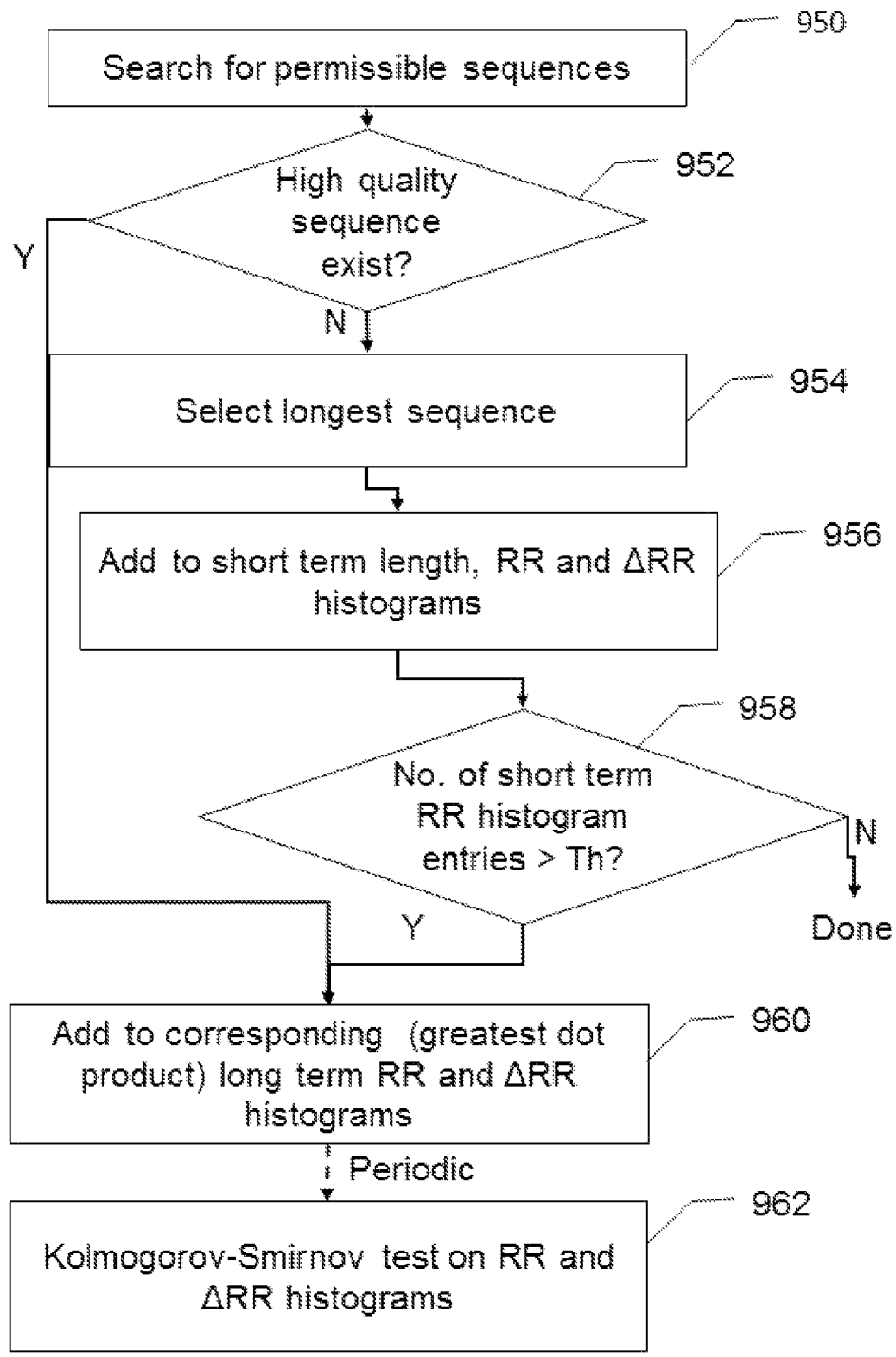
FIG. 13 is a flowchart of a routine for detecting atrial fibrillation.

FIG. 13 is a block diagram of an atrial fibrillation detection routine. Block 950 performs a search for physiologically permissible sequences within P(t,N).

The following describes a possible search technique for locating permissible sequences within the N beats in a segment. All permissible peak pairs within P(t,N) are determined. For example, assume that the first peak in a sequence occurs at 100 ms, and the next 4 peaks occur at 300 ms, 700 ms, 1000 ms, and 1700 ms, If the minimum permissible RR interval is 300 ms and the maximum permissible RR interval is 1700 ms, then the peak pairs that include the first beat are [1,3] and [1,4]. Pair [1,2] is excluded because its associated RR interval, 200 ms, is too short. Similarly, peak 1 cannot pair with peak 5 or beyond since the associated RR intervals are too long.

Starting with the first unprocessed pair, all subsequences that start with that pair are located. A subsequence is a continuous string of peaks whose associated RR intervals fall within the permissible ranges, and in which the change in RR interval between successive pairs does not exceed a threshold (e.g. 400 ms).

The subsequences may be stored in a tree like structure to efficiently perform the search. Continuing with the above example, assume that [3 5], [3 6] and [3 7] are permissible peak pairs, and that the RR intervals for [3 5] and [3 6] are less than the threshold amount (e.g. 400 ms) different than the RR interval for [1 3], but the RR interval for [3 7] is more than the threshold amount (e.g. 400 ms) different than the RR interval for [1 3]. There are thus two branches to the search beginning with [1 3], namely the branches [3 5] and [3 6]. Subsearches are performed at each branch beat up and down the tree structure to complete the search. Any peak pair that is part of the search tree is marked as processed. Step 2 is then repeated until the entire search is complete.

The above search procedure may result in non-overlapping subsequences of peaks. For example, two permissible sequences may be [1 4 7 11] and [15 16 19]. Even though merging the two subsequence would result in a gap (between peaks 11 and 15) that is not permissible according to the RR criteria, the total sequence [1 4 7 11 15 16 19] still needs to be considered because it still may be legitimate despite having a few gaps. On the other hand, merging all non-overlapping subsequences unnecessarily expands the number of total sequences, which is not optimal from a computational/memory standpoint. Thus, only "good" subsequences are merged, meaning sequences characterized by relatively smaller RR interval variability.

Block 952 determines whether any of the sequences have a high quality with respect to: 1) a high degree of RR interval order; and 2) signal to noise ratio, i.e., the sequence includes a subsequence that is a high SNR, incomplete group as determined by block 48, FIG. 3. A sequence can have a high degree of RR order even though it does not correspond to sinus rhythm. For example, a bigeminal rhythm is highly ordered. One way of assessing RR order is to determine the quality of at least 2 clusters (analogous to block 46 of FIG. 3) of a Poincare plot for the sequence.

If an ordered sequence does not exist, in block 954, the longest sequence (i.e., the one with the most number of peaks) is chosen. If there is a tie for longest sequence, the one with the smaller standard deviation is chosen. The length of the sequence is added to a short term length histogram, and short term histograms for RR and ΔRR are also incremented.

In block 958, the number of short term histogram entries is compared to a threshold, Th, which is preferably between 50 and 100. If the number of short term RR histogram entries exceeds the threshold, the short term histograms are cleared after being added to the long term histograms in block 960.

In block 960, the long term histograms that are updated with new data (either the short term histograms from block 958 or the single sequence histograms from block 952) is selected according to the best match between the new RR histogram (from either block 952 or 958) and long term RR histogram. The best match is determined by the maximum value of the dot product between the new RR histogram and the long term histogram. The RR histogram bins are preferably centered at [300:50:1200] (all these units are in ms). If the number of entries across these bins is defined as a vector N (which has 19 dimensions), and Na is the vector representing the new RR histogram data and Nb is a vector representing one of the long term RR histograms, then b is chosen to maximize Na·Nb, provided that the dot product exceeds a threshold. If not, then a new long term histogram is initialized with the Na data.

Initially, there will not be any long term histograms with which to compare the new data. The very first new data forms the first long term histogram.

In block 962, a statistical test is performed on the histograms to assess the likelihood of atrial fibrillation. For example, FIG. 14 shows maximum sequence length histograms associated with pure noise and atrial fibrillation corrupted with noise. Specifically, plot 980 is a histogram of the maximum length sequences associated with pure noise (i.e. randomly generated peak times) in 10 second long segments, while plot 982 is a maximum length histogram of simulated atrial fibrillation corrupted with 15 noise spikes (again in a 10 second segment). The RR intervals in simulated atrial fibrillation were generated according to 350 ms+X*850 ms, where X was a random number within [0,1]. As can be seen by comparing the plots, there is a distinct difference in the distribution of maximum sequence durations between pure noise and the simulated atrial fibrillation corrupted with noise.

FIG. 16 shows a plots of the maximum and minimum slopes of true peaks and noise peaks, along with lines that show a measure of feature space separation, which may be used to both perform clustering and calculate the clustering based signal to noise ratio (blocks 44 and 46, FIG. 3). Lines 1000 and 1002 are oriented at 45 degrees. A measure of cluster quality is based on the distance between the lines 1000 and 1002 and the number of points within each of the three sectors ("above" line 1000, between lines 1000 and 1002, and "below" line 1002). 45 degree lines may be calculated for each peak, and the best clustering determined according to the above mentioned cluster quality, which is also the signal to noise ratio calculated in block 46 of FIG. 3.

In three and higher dimensional feature spaces, planes and hyper-planes will replace lines. The 45 degree angles of lines 1000 and 1002 were appropriate for noise peaks caused by motion artifact, at least according to some data. Other angles may be appropriate for noise associated with other data. The best angle (in the case of a 2-D feature space) or plane/hyperplane orientation (in the case of 3-D or higher order feature spaces) may be determined for other data sets by extracting the features associated with noise peaks and, analogously to FIG. 16, determining optimal angles/orientations.

The overall size and shape of the (possibly) true peak cluster may also contribute to the calculation of the signal to noise ratio. More generally, other measures of cluster quality, e.g. Davies-Bouldin index and the Dunn index, may be used to calculate the signal to noise ratio.

What is claimed is:

1. A method for detecting heartbeats comprising the steps of:
   receiving an analog cardiac signal from a sensor;
   converting the analog signal to a digital signal,
   storing the digital signal in a digital memory, thereby creating a stored digital signal;
   detecting a plurality of peaks within a segment of the stored digital signal such that it is possible for the period between least two of the peaks to be less than the refractory period for human heart beats;
   searching within a subset of the plurality of peaks for a set of physiologically permissible sequences;
   assigning a score to each of a subset of the set of physiologically permissible sequences, wherein the score is based on a probability measure; and
   selecting a sequence with the highest score, thereby detecting a plurality of heart beats;
   wherein the steps of detecting, searching, assigning and selecting are performed by a digital processor.

2. The method of claim 1 wherein the probability measure is based on the time between adjacent peaks in sequence.

3. The method of claim 2 wherein the probability measure is based on a priori RR interval statistics.

4. The method of claim 3 wherein the a priori RR interval statistics pertain to the change in RR intervals.

5. The method of claim 1 wherein the probability measure is based on a peak shape feature.

6. The method of claim 1 wherein the sensor is an electrode.

7. The method of claim 1 wherein the subset of the plurality of peaks consists of the N largest sloped peaks within the detected peaks, wherein largest is an absolute value measure.

8. The method of claim 1 wherein each of the set of physiologically permissible sequences is indicative of sinus rhythm.

9. The method of claim 8 wherein the search is performed by locating peaks that are separated by a time that when divided by a specified RR interval, is equal to one of a set of positive integers, plus or minus a specified tolerance.

10. The method of claim 9 wherein the set of positive integers includes integers greater than one, thereby permitting skipped beats.

11. The method of claim 9 wherein the specified RR interval is the time between two test peaks in the subset, and wherein the search is performed on the peaks in the subset outside of the time interval defined by the two test peaks.

\* \* \* \* \*